United States Patent [19]

Mori et al.

[11] Patent Number: 5,035,881

[45] Date of Patent: Jul. 30, 1991

[54] DENTIFRICE COMPOSITION

[75] Inventors: Shigeki Mori; Chiho Makino, both of Takatsuki, Japan

[73] Assignee: Sunstar Kabushiki Kaisha, Osaka, Japan

[21] Appl. No.: 509,344

[22] Filed: Apr. 16, 1990

[30] Foreign Application Priority Data

Apr. 24, 1989 [JP] Japan ................. 1-104151

[51] Int. Cl.$^5$ ................. A61K 7/22; A61K 7/16
[52] U.S. Cl. .................. 424/54; 424/49
[58] Field of Search ................. 424/49, 52, 54

[56] References Cited

U.S. PATENT DOCUMENTS

| | | | |
|---|---|---|---|
| 3,842,168 | 10/1974 | Colodney | 424/52 |
| 3,843,779 | 10/1974 | Norfleet | 424/54 |
| 3,927,201 | 12/1975 | Baines et al. | 424/54 |
| 3,934,002 | 1/1976 | Haefele | 424/54 |
| 3,937,805 | 2/1976 | Harrison | 424/52 |
| 3,989,813 | 11/1976 | Januszewski et al. | 424/54 |
| 4,025,616 | 5/1977 | Haefele | 424/52 |
| 4,051,234 | 9/1977 | Gieske et al. | 424/52 |
| 4,059,624 | 11/1977 | Harrison | 424/54 |
| 4,110,083 | 8/1978 | Benedict | 424/54 |
| 4,157,387 | 6/1979 | Benedict | 424/54 |
| 4,160,822 | 7/1979 | Hashimoto et al. | 424/52 |
| 4,238,476 | 12/1980 | Harvey | 424/52 |
| 4,241,049 | 12/1980 | Colodney et al. | 424/54 |
| 4,407,788 | 10/1983 | Kiozpeoplou | 424/49 |
| 4,545,979 | 10/1985 | Ambike et al. | 424/52 |
| 4,618,488 | 10/1986 | Maeyama et al. | 424/49 |
| 4,657,758 | 4/1987 | Goldemberg et al. | 424/49 |
| 4,661,342 | 4/1987 | Yamazaki et al. | 424/54 |
| 4,828,824 | 5/1989 | Grullier | 424/52 |

FOREIGN PATENT DOCUMENTS 2149661 6/1985 United Kingdom .

Primary Examiner—Shep K. Rose
Attorney, Agent, or Firm—Wegner, Cantor, Mueller & Player

[57] ABSTRACT

A dentifrice composition containing a bactericide selected from the group consisting of biguanido bactericides and N-alkyldiaminoethylglycine, a polyoxyethylenepolyoxypropylene block copolymer surfactant and a N-higher acylamino acid or its salt is disclosed. The dentifrice composition maintains bactericidal activities of the bactericide added.

4 Claims, No Drawings

DENTIFRICE COMPOSITION

FIELD OF THE INVENTION

The present invention relates to a dentifrice composition containing a biguanido bactericide and/or N-alkyldiaminoethylglycine without any binder. The dentifrice composition of the present invention maintains the stability of bactericidal activities of the bactericide contained therein and has excellent foaming properties.

BACKGROUND OF THE INVENTION

A biguanido bactericide or N-alkyldiaminoethylglycine (hereinafter generally referred to as bactericide) is effective for inhibition of the formation of dental plaque and has hitherto been added to dentifrices. On the other hand, in general, a foaming agent (surfactant) and a binder to be added to dentifrices are anionic ingredients. Then, the bactericide reacts with these ingredients to form a complex, which results in remarkable loss of bactericidal activities of the bactericide added. Therefore, there is a problem that, even when bactericide is added in order to inhibit the formation of dental plaque, in practice, its effect can scarcely be expected.

For solving such a problem, a composition employing a nonionic surfactant as a foaming agent is disclosed in U.S. Pat. Nos. 4,080,441, 4,110,429 and 4,118,476 as well as British Patent No. 1,573,356. However, there is another problem that, although such a composition maintains bactericidal activities, its foaming properties and feeling for use are deteriorated.

OBJECTS OF THE INVENTION

Under these circumstances, the present inventors have intensively studied to solve above problems. As a result, it has been found that, using a specific surfactant, a dentifrice composition which maintains the stability of bactericidal activities of the bactericide added and has excellent foaming properties can be obtained without using any binder.

The main object of the present invention is to provide a dentifrice composition which maintains stable bactericidal activities and has excellent foaming properties.

This object as well as other objects and advantages of the present invention will become apparent to those skilled in the art from the following description.

SUMMARY OF THE INVENTION

According to the present invention, there is provided a dentifrice composition which comprises a bactericide selected from the group consisting of biguanido bactericides and N-alkyldiaminoethylglycine, a polyoxyethylene-polyoxypropylene block copolymer surfactant and a N-higher acylamino acid or its salt. According to the present invention, loss of bactericidal activities of the bactericide added is efficiently prevented and, therefore, inhibition of the formation of dental plaque as well as the prevention of gingivitis can be efficiently conducted. In the present invention, since the block copolymer surfactant is capable of gelation, excellent shape retention can be maintained without addition of any binder.

DETAILED DESCRIPTION OF THE INVENTION

As the biguanido bactericides to be used in the present invention, there are chlorhexidine hydrochloride, chlorhexidine gluconate, chlorhexidine acetate, 1,6-bis-(2-ethylhexyl biguanidohexane)dihydrochloride and the like. As N-alkyldiaminoethylglycine, there are N-($C_{12}$ to $C_{18}$)-alkylaminoethylglycine. Examples thereof include N-lauryldiaminoethylglycine, N-myristyldiaminoethylglycine, N-($C_{12}$ to $C_{14}$)alkylaminoethylglycine and the like. These bactericides can be used alone or in combination thereof. Although the amount of bactericide to be added is not specifically limited, normally, it is 0.001 to 0.5% by weight based on the total weight of the dentifrice composition in view of bactericidal activities and economy.

The polyoxyethylene-polyoxypropylene block copolymer surfactant to be used in the present invention is polyoxyethylene-polyoxypropylene glycol represented by the general formula:

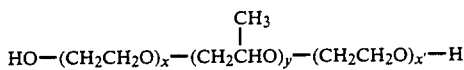

wherein x, x' and y are integers, or
a polyoxyethylene-polyoxypropylene glycol addition compound of ethylenediamine represented by the general formula:

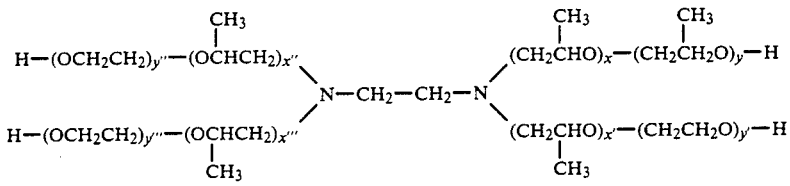

wherein x, x', x'', x''', y, y', y'' and y''' are integers.

Such a block copolymer is commercially available under the trade name of "PLURONIC" or "TETRONIC" manufactured by BASF Corporation, U.S.A. In general, the copolymer is chemically defined according to the molecular weight of its hydrophobic portion composed of polyoxypropylene and the proportion (% by weight) of its hydrophilic portion composed of polyoxyethylene in the molecule. Preferred polyoxyethylene-polyoxypropylene glycol has the molecular weight of the hydrophobic group (polyoxypropylene) of 1,400 to 4,000 and contains 30 to 80% by weight of the hydrophilic group (polyoxyethylene) in the molecule. Further, the preferred polyoxyethylenepolyoxypropylene glycol addition compound of ethylenediamine has the molecular weight of the hydrophobic group (polyoxypropylene) of 4,500 to 7,000 and contains 40 to 90% by weight of the hydrophilic group (polyoxyethylene) in the molecule. The polyoxyethylene-polyoxypropylene block copolymer surfactant can be added to the composition in an amount of about 11 to 80% by weight, preferably 15 to 40% by weight based on the total weight of the dentifrice composition. When the amount of the surfactant added is less than 11% by weight, a problem in form stability due to syneresis is caused because of insufficient gelation. On the other hand, when the amount exceeds 80% by weight, gelation is too strong to obtain a suitable viscosity as a dentifrice.

As the N-higher acylamino acid or salt thereof to be used in the present invention, there are N-($C_{12}$ to $C_{18}$)-acylamino acids and alkali metal salts thereof. Examples thereof include sodium N-lauroyl glutamate, sodium N-lauroyl sarcosinate, sodium N-myristoyl sarcosinate, N-oleoyl sarcosinate, sodium lauroyl methylalanine and the like. Such a compound can be used alone or in combination thereof. The amount of the compound added is normally 0.01 to 5% by weight, preferably 0.1 to 3% by weight based on the total weight of the dentifrice composition. When the amount is less than 0.01% by weight, the improvement of foaming properties can scarcely be expected and, when the amount exceeds 5% by weight, a problem in safety for oral mucosa such as detachment of oral mucosa and the like is caused.

The dentifrice composition of the present invention can be prepared in the form of toothpaste, pasta and the like according to the conventional production process. Further, in so far as the effect of the present invention is not damaged, appropriate ingredients, for example, polishing agents such as calcium secondary phosphate anhydride or dihydrate, calcium carbonate, calcium pyrophosphate, insoluble sodium metaphosphate, aluminum hydroxide, aluminum oxide, a resin and the like; humectants such as polyethylene glycol, sorbitol, glycerin, propylene glycol and the like; essential oils such as peppermint, spearmint and the like; flavors such as l-menthol, carvone, anethole and the like; sweeteners such as saccharin sodium, stevioside, neohesperidyl hydrocharcone, glycyrrhizin, perillartin, p-methoxycinnamic aldehyde, thaumatin and the like; pharmacologically active ingredients such as sodium monofluorophosphate, sodium fluoride, dextranase, mutanase, hinokitiol, allantoin, ,-aminocaproic acid, tranexamic acid, azulene, vitamin E derivatives, sodium chloride and the like can be added at need.

As described above, the dentifrice composition of the present invention maintains the stability of bactericidal activities. Therefore, it can effectively inhibit the formation of dental plaque and prevent gingivitis.

The following Examples and Comparative Examples further illustrate the present invention in detail but are not to be construed to limit the scope thereof. In the Examples and Comparative Examples, all the percents are by weight unless otherwise stated.

EXAMPLES 1 TO 12 AND COMPARATIVE EXAMPLES 1 TO 28

Using the formulations as shown in Tables 1 to 4, toothpastes were prepared according to the conventional method.

Bactericidal activities and foaming properties of the toothpastes thus obtained were determined by the following methods.

Bactericidal Activity Test

Each toothpaste (about 6.0 g) was weighed and suspended in distilled water. The suspension was centrifuged to obtain the supernatant. The supernatant was diluted with distilled water so that the concentration of bactericide in the supernatant became 0.05%, 0.10% and 0.20% in the case of chlorhexidine gluconate, or 0.001%, 0.002% and 0.004% in the case of N-($C_{12}$ to $C_{14}$)alkyldiamioethylglycine hydrochloride (TEGO 51 manufactured by Goldschmidt Corp.).

On the other hand, chlorhexidine gluconate or diaminoethyl glycine hydrochloride was dissolved in distilled water so that the concentration thereof became 0.05%, 0.10% and 0.20% in the case of the former, or 0.001%, 0.002% and 0.004% in the case of the latter. These solutions were used as standard solutions for the determination of minimum bactericidal concentration (%, hereinafter abbreviated as MBC).

To each sample (10 ml) was added $10^8$ to $10^9$ CFU/ml of a *Streptococcus mutans* cell suspension (0.1 ml) and a bactericidal reaction was carried out in a water bath at 37° C. for 15 minutes. After completion of the reaction, one loopful of each sample was spread on a trypticase soy agar (TSA) plate containing 0.5% of polyoxyethylene monooleate and 0.07% of lecithin. Then, it was incubated at 37° C. for 2 days under anaerobic conditions ($N_2/H_2/CO_2 = 85/10/5$) and MBC was determined.

MBC of the standard solutions were 0.05% for chlorohexidine gluconate and 0.001% for N-($C_{12}$ to $C_{14}$)alkyldiaminoethylglycine hydrochloride (TEGO 51).

The samples were evaluated according to the following criteria.

A: MBC of the sample tested was the same as that of the standard solution [chlorhexidine glutamate: 0.05%, N-($C_{12}$ to $C_{14}$)alkylaminoethylglycine hydrochloride (TEGO 51): 0.01%].

B: MBC of the sample tested was greater than that of the standard solution.

Foaming test

The toothpaste to be tested was diluted three times with distilled water and the diluted solution (100 ml) was placed in a measuring cylinder (innet diameter: 6.5 mm) and stirred in a water bath at 30° C. for 3 minutes by using a contrarotation stirrer (1000 r.p.m., contrarotating every 6 seconds, four bladed screw, 5.0 mm in diameter). The foaming volume was expressed by the difference between the apparent volume just after stirring and the volume of diluted solution before stirring as follows.

Foaming volume (ml) = Apparent volume just after stirring (ml) − Volume of diluted solution before stirring (ml)

Overall Evaluation

Overall evaluation was conducted according to the following criteria.

A: Evaluation of bactericidal activities was A and the foaming volume was not less than 180 ml.

B: At least, evaluation of bactericidal activities was B or the foaming volume was less than 180 ml.

The results are shown in Tables 1 to 4. In the following Tables. 1 to 4, all the amount of ingredients added are % by weight.

TABLE 1

| Ingredients (Additives) | Example No. 1 | Example No. 2 | Example No. 3 | Comparative Example No. 1 | Comparative Example No. 2 | Comparative Example No. 3 | Comparative Example No. 4 | Comparative Example No. 5 | Comparative Example No. 6 | Comparative Example No. 7 |
|---|---|---|---|---|---|---|---|---|---|---|
| Sodium N-lauroyl-glutamate | 0.5 | — | — | — | — | — | — | — | — | — |
| Sodium N-lauroyl-sarcosinate | — | 0.5 | — | — | — | — | — | — | — | — |
| Sodium N-lauroyl-methylalanine | — | — | 0.5 | — | — | — | — | — | — | — |
| Sodium N-lauroyl-methyltaurin | — | — | — | 0.5 | — | — | — | — | — | — |
| Sodium lauryl phosphate | — | — | — | — | 0.5 | — | — | — | — | — |
| Sodium α-olefin sulfonate | — | — | — | — | — | 0.5 | — | — | — | — |
| Polyoxyethylene hydrogenated castor oil (60 E.O.) | — | — | — | — | — | — | 0.5 | — | — | — |
| Sucrose fatty acid ester | — | — | — | — | — | — | — | 0.5 | — | — |
| Sodium caseinate | — | — | — | — | — | — | — | — | 0.5 | — |
| Polyoxyethylene (196)* polyoxypropylene glycol (67)* | 20.0 | 20.0 | 20.0 | 20.0 | 20.0 | 20.0 | 20.0 | 20.0 | 20.0 | 20.0 |
| Chlorhexidine gluconate | 0.2 | 0.2 | 0.2 | 0.2 | 0.2 | 0.2 | 0.2 | 0.2 | 0.2 | 0.2 |
| Calcium hydrogen-phosphate anhydride | 20.0 | 20.0 | 20.0 | 20.0 | 20.0 | 20.0 | 20.0 | 20.0 | 20.0 | 20.0 |
| Glycerin | 10.0 | 10.0 | 10.0 | 10.0 | 10.0 | 10.0 | 10.0 | 10.0 | 10.0 | 10.0 |
| Saccharin sodium | 0.3 | 0.3 | 0.3 | 0.3 | 0.3 | 0.3 | 0.3 | 0.3 | 0.3 | 0.3 |
| Flavor | 1.0 | 1.0 | 1.0 | 1.0 | 1.0 | 1.0 | 1.0 | 1.0 | 1.0 | 1.0 |
| Distilled water | | | | | (up to 100%) | | | | | |
| Bactericidal Activities | A | A | A | B | B | B | B | B | B | A |
| Foaming volume (ml) | 220 | 210 | 200 | 200 | 200 | 190 | 170 | 160 | 160 | 150 |
| Overall evaluation | A | A | A | B | B | B | B | B | B | B |

Note
*The number in the parentheses means the average polymerization degree

TABLE 2

| Ingredients (Additive) | Example No. 4 | Example No. 5 | Example No. 6 | Comparative Example No. 8 | Comparative Example No. 9 | Comparative Example No. 10 | Comparative Example No. 11 | Comparative Example No. 12 | Comparative Example No. 13 | Comparative Example No. 14 |
|---|---|---|---|---|---|---|---|---|---|---|
| Sodium N-lauroyl-glutamate | 0.5 | — | — | — | — | — | — | — | — | — |
| Sodium N-lauroyl-sarcosinate | — | 0.5 | — | — | — | — | — | — | — | — |
| Sodium N-lauroyl-methylalanine | — | — | 0.5 | — | — | — | — | — | — | — |
| Sodium N-lauroyl-methyltaurin | — | — | — | 0.5 | — | — | — | — | — | — |
| Sodium lauryl phosphate | — | — | — | — | 0.5 | — | — | — | — | — |
| Sodium α-olefin sulfonate | — | — | — | — | — | 0.5 | — | — | — | — |
| Polyoxyethylene hydrogenated castor oil (60 E.O.) | — | — | — | — | — | — | 0.5 | — | — | — |
| Sucrose fatty acid ester | — | — | — | — | — | — | — | 0.5 | — | — |
| Sodium caseinate | — | — | — | — | — | — | — | — | 0.5 | — |
| Polyoxyethylene (196)* polyoxypropylene glycol (67)* | 20.0 | 20.0 | 20.0 | 20.0 | 20.0 | 20.0 | 20.0 | 20.0 | 20.0 | 20.0 |
| Alkyldiamino ethyl glycine hydrochloride | 0.2 | 0.2 | 0.2 | 0.2 | 0.2 | 0.2 | 0.2 | 0.2 | 0.2 | 0.2 |
| Calcium hydrogen-phosphate anhydride | 20.0 | 20.0 | 20.0 | 20.0 | 20.0 | 20.0 | 20.0 | 20.0 | 20.0 | 20.0 |
| Glycerin | 10.0 | 10.0 | 10.0 | 10.0 | 10.0 | 10.0 | 10.0 | 10.0 | 10.0 | 10.0 |
| Saccharin sodium | 0.3 | 0.3 | 0.3 | 0.3 | 0.3 | 0.3 | 0.3 | 0.3 | 0.3 | 0.3 |
| Flavor | 1.0 | 1.0 | 1.0 | 1.0 | 1.0 | 1.0 | 1.0 | 1.0 | 1.0 | 1.0 |
| Distilled water | | | | | (up to 100%) | | | | | |
| Bactericidal Activities | A | A | A | B | B | B | B | B | B | A |
| Foaming volume (ml) | 220 | 215 | 200 | 200 | 195 | 190 | 165 | 160 | 160 | 150 |

TABLE 2-continued

| Ingredients | Example No. | | | Comparative Example No. | | | | | | |
|---|---|---|---|---|---|---|---|---|---|---|
| (Additive) | 4 | 5 | 6 | 8 | 9 | 10 | 11 | 12 | 13 | 14 |
| Overall evaluation | A | A | A | B | B | B | B | B | B | B |

Note
*The number in the parentheses means the average polymerization degree.

TABLE 3

| Ingredients | Example No. | | | Comparative Example No. | | | | | | |
|---|---|---|---|---|---|---|---|---|---|---|
| (Additive) | 7 | 8 | 9 | 15 | 16 | 17 | 18 | 19 | 20 | 21 |
| Sodium N-lauroyl-glutamate | 0.5 | — | — | — | — | — | — | — | — | — |
| Sodium N-lauroyl-sarcosinate | — | 0.5 | — | — | — | — | — | — | — | — |
| Sodium N-lauroyl-methylalanine | — | — | 0.5 | — | — | — | — | — | — | — |
| Sodium N-lauroyl-methyltaurin | — | — | — | 0.5 | — | — | — | — | — | — |
| Sodium lauryl phosphate | — | — | — | — | 0.5 | — | — | — | — | — |
| Sodium α-olefin sulfonate | — | — | — | — | — | 0.5 | — | — | — | — |
| Polyoxyethylene hydrogenated castor oil (60 E.O.) | — | — | — | — | — | — | 0.5 | — | — | — |
| Sucrose fatty acid ester | — | — | — | — | — | — | — | 0.5 | — | — |
| Sodium caseinate | — | — | — | — | — | — | — | — | 0.5 | — |
| Ethylenediamine-polyoxyethylene (296)* polyoxypropylene glycol (92)* addition compound | 20.0 | 20.0 | 20.0 | 20.0 | 20.0 | 20.0 | 20.0 | 20.0 | 20.0 | 20.0 |
| Chlorhexidine gluconate | 0.2 | 0.2 | 0.2 | 0.2 | 0.2 | 0.2 | 0.2 | 0.2 | 0.2 | 0.2 |
| Calcium hydrogenphosphate anhydride | 20.0 | 20.0 | 20.0 | 20.0 | 20.0 | 20.0 | 20.0 | 20.0 | 20.0 | 20.0 |
| Glycerin | 10.0 | 10.0 | 10.0 | 10.0 | 10.0 | 10.0 | 10.0 | 10.0 | 10.0 | 10.0 |
| Saccharin sodium | 0.3 | 0.3 | 0.3 | 0.3 | 0.3 | 0.3 | 0.3 | 0.3 | 0.3 | 0.3 |
| Flavor | 1.0 | 1.0 | 1.0 | 1.0 | 1.0 | 1.0 | 1.0 | 1.0 | 1.0 | 1.0 |
| Distilled water | (up to 100%) | | | | | | | | | |
| Bactericidal Activities | A | A | A | B | B | B | B | B | B | A |
| Foaming volume (ml) | 210 | 205 | 200 | 190 | 185 | 180 | 165 | 155 | 150 | 140 |
| Overall evaluation | A | A | A | B | B | B | B | B | B | B |

Note
*The number in the parentheses means the average polymerization degree.

TABLE 4

| Ingredients | Example No. | | | Comparative Example No. | | | | | | |
|---|---|---|---|---|---|---|---|---|---|---|
| (Additive) | 10 | 11 | 12 | 22 | 23 | 24 | 25 | 26 | 27 | 28 |
| Sodium N-lauroyl-glutamate | 0.5 | — | — | — | — | — | — | — | — | — |
| Sodium N-lauroyl-sarcosinate | — | 0.5 | — | — | — | — | — | — | — | — |
| Sodium N-lauroyl-methylalanine | — | — | 0.5 | — | — | — | — | — | — | — |
| Sodium N-lauroyl-methyltaurin | — | — | — | 0.5 | — | — | — | — | — | — |
| Sodium lauryl phosphate | — | — | — | — | 0.5 | — | — | — | — | — |
| Sodium α-olefin sulfonate | — | — | — | — | — | 0.5 | — | — | — | — |
| Polyoxyethylene hydrogenated castor oil (60 E.O.) | — | — | — | — | — | — | 0.5 | — | — | — |
| Sucrose fatty acid ester | — | — | — | — | — | — | — | 0.5 | — | — |
| Sodium caseinate | — | — | — | — | — | — | — | — | 0.5 | — |
| Ethylenediamine-polyoxyethylene (296)* polyoxypropylene glycol (92)* addition compound | 20.0 | 20.0 | 20.0 | 20.0 | 20.0 | 20.0 | 20.0 | 20.0 | 20.0 | 20.0 |
| TEGO 51 | 0.2 | 0.2 | 0.2 | 0.2 | 0.2 | 0.2 | 0.2 | 0.2 | 0.2 | 0.2 |

TABLE 4-continued

| Ingredients (Additive) | Example No. | | | Comparative Example No. | | | | | | |
|---|---|---|---|---|---|---|---|---|---|---|
| | 10 | 11 | 12 | 22 | 23 | 24 | 25 | 26 | 27 | 28 |
| Calcium hydrogenphosphate anhydride | 20.0 | 20.0 | 20.0 | 20.0 | 20.0 | 20.0 | 20.0 | 20.0 | 20.0 | 20.0 |
| Glycerin | 10.0 | 10.0 | 10.0 | 10.0 | 10.0 | 10.0 | 10.0 | 10.0 | 10.0 | 10.0 |
| Saccharin sodium | 0.3 | 0.3 | 0.3 | 0.3 | 0.3 | 0.3 | 0.3 | 0.3 | 0.3 | 0.3 |
| Flavor | 1.0 | 1.0 | 1.0 | 1.0 | 1.0 | 1.0 | 1.0 | 1.0 | 1.0 | 1.0 |
| Distilled water | | | | | (up to 100%) | | | | | |
| Bactericidal Activity | A | A | A | B | B | B | B | B | B | A |
| Foaming volume (ml) | 210 | 205 | 200 | 190 | 180 | 175 | 160 | 150 | 150 | 140 |
| Overall evaluation | A | A | A | B | B | B | B | B | B | B |

Note
*The number in the parentheses means the average polymerization degree.

As shown in Tables 1 to 4, by using biguanido bactericides or N-alkyldiaminoethylglycine in combination with the polyoxyethylene polyoxypripylene block copolymer, surfactant and N-higher acylamino acid or salt thereof, good foaming properties was obtained without loss of bactericidal activities of the bactericide added.

EXAMPLE 13

Using the following formulation, a toothpaste was prepared according to the conventional method.

| Ingredients | % by weight |
|---|---|
| Chlorhexidine hydrochloride | 0.2 |
| PLURONIC ® F88 | 30.0 |
| average polymerization degree | |
| ethylene oxide: 194 | |
| propylene oxide: 39 | |
| Sodium N-lauroylsarcosinate | 0.5 |
| Calcium hydrogenphosphate anhydride | 20.0 |
| Glycerin | 10.0 |
| saccharin sodium | 0.3 |
| Flavor | 1.0 |
| Sodium monofluorophosphate | 0.8 |
| Distilled water | up to 100% |

EXAMPLE 14

Using the following formulation, a toothpaste was prepared to the conventional method.

| Ingredients | % by weight |
|---|---|
| Alexidine | 0.5 |
| TETRONIC ® F1307 | 20.0 |
| average polymerization degree | |
| ethylene oxide: 296 | |
| propylene oxide: 92 | |
| Sodium N-lauroyl glutamate | 1.0 |
| Aluminum oxide | 10.0 |
| Sorbitol | 20.0 |
| Dipotassium glycyrrhizinate | 0.2 |
| Flavor | 0.8 |
| Distilled water | up to 100% |

EXAMPLE 15

Using the following formulation, a toothpaste was prepared according to the conventional method.

| Ingredients | % by weight |
|---|---|
| N-myristyldiaminoethyl glycine | 0.1 |
| PLURONIC ® F85 | 35.0 |
| average polymerization degree | |
| ethylene oxide: 42 | |
| propylene oxide: 47 | |
| Sodium N-lauroylmethylalanine | 0.5 |
| Calcium carbonate | 25.0 |
| Propylene glycol | 10.0 |
| Stevioside | 0.4 |
| Flavor | 0.9 |
| Allantoin | 0.1 |
| Distilled water | up to 100% |

EXAMPLE 16

Using the following formulation, a toothpaste was prepared according to the conventional method.

| Ingredients | % by weight |
|---|---|
| Chlorhexidine acetate | 0.2 |
| PLURONIC ® F87 | 25.0 |
| average polymerization degree | |
| ethylene oxide: 124 | |
| propylene oxide: 39 | |
| Sodium N-myristoyl glutamate | 0.5 |
| Aluminum hydroxide | 25.0 |
| Polyethylene glycol | 8.0 |
| Saccharin sodium | 0.4 |
| Flavor | 1.0 |
| Azulene | 0.2 |
| Distilled water | up to 100% |

All the compositions of Examples 13 to 16 has good bactericidal activities and foaming properties.

What is claimed is:

1. A dentifrice composition which is a foaming bactericidal toothpaste, free of any binder and comprises (A) 0.001 to 0.5% by weight of biguanido bactericide or N-alkyldiaminoethylglycine bactericide, (B) not less than about 11% by weight to n to more than 80% by weight of polyoxyethylene-polyoxypropylene block copolymer surfactant, and (C) 0.01 to 5% by weight of a foaming N-higher acylamino acid or salt thereof.

2. A dentifrice composition according to claim 1, wherein the biguanido bactericide is selected from the group consisting of chlorohexidine hydrochloride, chlorohexidine gluconate, chlorhexidine acetate and 1,6-bis-(2-ethylhexyl biguanidohexane)dihydrochloride.

3. A dentifrice composition according to claim 1, wherein the N-alkyldiaminoethylglycine is N-($C_{12}$ to $C_{18}$)-dialkylaminoethylglycine.

4. A dentifrice composition according to claim 1, wherein the N-higher acylamino acid or salt thereof is an N-($C_{12}$ to $C_{18}$) acylamino acid or an alkali metal salt thereof.

* * * * *